(12) United States Patent
Yamamoto et al.

(10) Patent No.: US 8,481,744 B2
(45) Date of Patent: Jul. 9, 2013

(54) PROCESS FOR PRODUCING ANTHRANILAMIDE COMPOUND

(75) Inventors: Kazuhiro Yamamoto, Kusatsu (JP); Tetsuo Yoneda, Kusatsu (JP); Fumio Kanamori, Kusatsu (JP); Shigehisa Kanbayashi, Kusatsu (JP); Toyoshi Tanimura, Kusatsu (JP); Yohei Taguchi, Osaka (JP); Tatsunori Yoshida, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 220 days.

(21) Appl. No.: 12/937,647

(22) PCT Filed: Apr. 10, 2009

(86) PCT No.: PCT/JP2009/057393
§ 371 (c)(1),
(2), (4) Date: Oct. 13, 2010

(87) PCT Pub. No.: WO2009/128408
PCT Pub. Date: Oct. 22, 2009

(65) Prior Publication Data
US 2011/0034696 A1 Feb. 10, 2011

(30) Foreign Application Priority Data

Apr. 16, 2008 (JP) .................. 2008-106657

(51) Int. Cl.
*C07D 401/04* (2006.01)
(52) U.S. Cl.
USPC ....................... 546/275.4
(58) Field of Classification Search
USPC ....................... 546/275.4
See application file for complete search history.

(56) References Cited

U.S. PATENT DOCUMENTS

| 8,115,006 B2 * | 2/2012 | Koyanagi et al. ......... 546/275.4 |
| 2004/0198984 A1 | 10/2004 | Lahm et al. |
| 2005/0215798 A1 | 9/2005 | Annis |
| 2006/0111403 A1 | 5/2006 | Hughes et al. |
| 2007/0129407 A1 | 6/2007 | Koyanagi et al. |

FOREIGN PATENT DOCUMENTS

| JP | 2005 502658 | 1/2005 |
| JP | 2005 534685 | 11/2005 |
| JP | 2006 515602 | 6/2006 |
| WO | 03 016283 | 2/2003 |
| WO | 2004 011453 | 2/2004 |
| WO | 2005 077934 | 8/2005 |
| WO | 2008 072745 | 6/2008 |

OTHER PUBLICATIONS

International Search Report issued Jul. 7, 2009 in PCT/JP09/57393 filed Apr. 10, 2009.

* cited by examiner

*Primary Examiner* — Patricia L Morris
(74) *Attorney, Agent, or Firm* — Oblon, Spivak, McClelland, Maier & Neustadt, L.L.P.

(57) ABSTRACT

To provide a process for producing an anthranilamide having the 3-position of pyrazole substituted by a bromine atom, or its salt.
A process for producing an anthranilamide compound represented by the formula (I) or its salt:

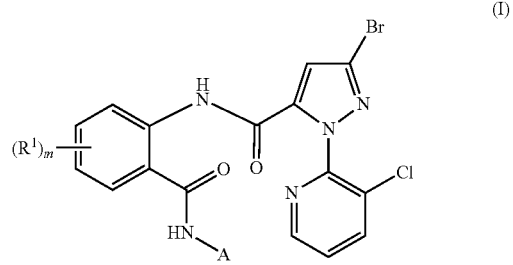

(I)

which comprises reacting a compound represented by the formula (II):

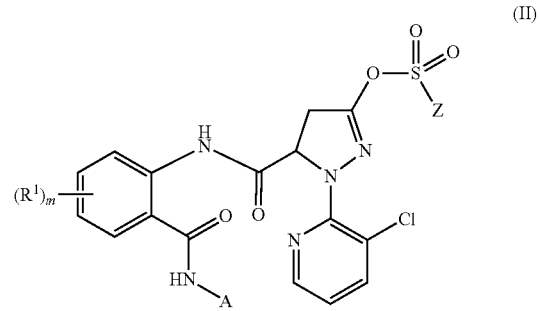

(II)

(wherein Z is 2-pyridyl, 3-pyridyl, 4-pyridyl or benzene substituted by a nitro group), with a brominating agent, to produce a compound represented by the formula (III):

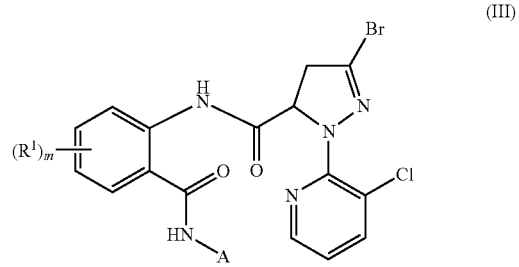

(III)

and further reacting the compound of the formula (III) with an oxidizing agent.

18 Claims, No Drawings

PROCESS FOR PRODUCING ANTHRANILAMIDE COMPOUND

CROSS-REFERENCE TO RELATED APPLICATIONS

This application is a National Stage of PCT/JP2009/057393 filed on Oct. 4, 2009. This is based upon and claims the benefit of priority to Japanese Application No. 2008-106657 filed on Apr. 16, 2008.

BACKGROUND OF THE INVENTION

1. Technical Field

The present invention relates to a process for producing an anthranilamide compound having a bromine atom at the 3-position of pyrazole.

2. Background Art

With respect to anthranilamide compounds, their excellent effects as pesticides in agricultural and horticultural fields are disclosed, for example, in Patent Document 1. Further, Patent Documents 2 and 3 disclose a process for producing a specific anthranilamide compound.

Patent Document 1: International Publication WO 2005/077934
Patent Document 2: International Publication WO 2003/016283
Patent Document 3: International Publication WO 2004/011453

DISCLOSURE OF THE INVENTION

Object to be Accomplished by the Invention

Heretofore, various processes have been proposed as processes for producing anthranilamide compounds. For bromination to produce an anthranilamide compound having the 3-position of pyrazole substituted by a bromine atom, there have been proposed, for example, a method wherein a hydroxypyrazoline compound is chlorinated by a highly toxic phosphorus-type chlorinating agent such as phosphorus oxychloride and then reacted with a brominating agent, and a method wherein a hydroxypyrazoline compound is converted to a specific sulfonic acid ester and then reacted with a brominating agent. However, the former method has a problem in safety by the use of a highly toxic phosphorus-type chlorinating agent. Whereas, by the latter method, the desired brominated product is obtainable in good yield only when the method is carried out under restricted conditions. Therefore, it is desired to develop a process for producing an anthranilamide compound having the 3-position of pyrazole substituted by a bromine atom, efficiently and inexpensively under commonly employed conditions.

It is an object of the present invention to provide a process for producing an anthranilamide compound having the 3-position of pyrazole substituted by a bromine atom under commonly employed conditions.

Means to Accomplish the Object

The present inventors have conducted an extensive study to solve the above problems and as a result, have found it possible to produce the desired compound in high yield even under commonly employed conditions, by introducing a highly detachable substituent at the 3-position of pyrazole, and thus, the present invention has been accomplished.

That is, the present invention relates to a process for producing an anthranilamide compound represented by the formula (I) or its salt:

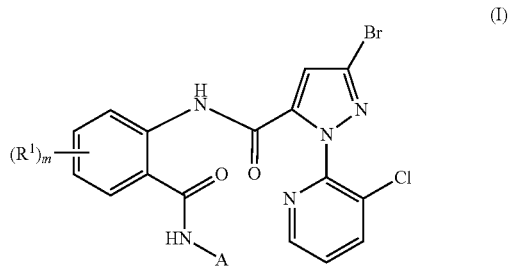

(I)

(wherein $R^1$ is halogen, alkyl, haloalkyl, alkenyl, haloalkenyl, alkynyl, haloalkynyl, alkoxy, haloalkoxy, alkylcarbonyl, haloalkylcarbonyl, alkoxycarbonyl, haloalkoxycarbonyl, nitro, formyl or cyano, A is alkyl which may be substituted by Y, Y is $C_{3-4}$ cycloalkyl which may be substituted by at least one substituent selected from the group consisting of halogen, alkyl and haloalkyl, and m is an integer of from 0 to 4), which comprises reacting a compound represented by the formula (II):

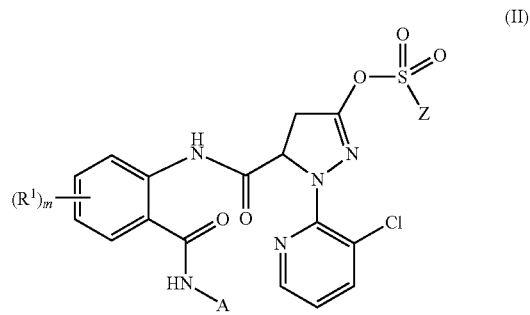

(II)

(wherein Z is 2-pyridyl, 3-pyridyl, 4-pyridyl or benzene substituted by a nitro group, and $R^1$, A and m are as defined above), with a brominating agent, to produce a compound represented by the formula (III):

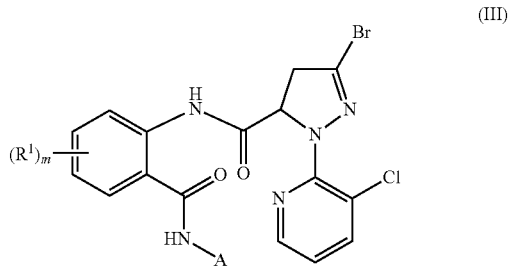

(III)

(wherein $R^1$, A and m are as defined above); and further reacting the compound of the formula (III) with an oxidizing agent to produce an anthranilamide compound of the above formula (I).

Further, the present invention relates to the compound of the above formula (II) as a raw material for the above process.

In each of the above formulae, the alkyl or alkyl moiety in $R^1$, A or Y may be linear or branched. Its specific example may, for example, be $C_{1-6}$ alkyl such as methyl, ethyl, propyl, isopropyl, butyl, tert-butyl, pentyl or hexyl.

The halogen or halogen as a substituent in $R^1$ or Y may be an atom of fluorine, chlorine, bromine or iodine. The number of halogens as substituents may be 1 or more, and if more, the respective halogens may be the same or different. Further, the positions for substitution of such halogens may be any positions.

The salt of the anthranilamide compound includes all kinds so long as they are agriculturally acceptable. It may, for example, be an alkali metal salt such as a sodium salt or a potassium salt; an alkaline earth metal salt such as a magnesium salt or a calcium salt; an ammonium salt such as a dimethylammonium salt or a triethylammonium salt; an inorganic acid salt such as a hydrochloride, a perchlorate, a sulfate or a nitrate; or an organic acid salt such as an acetate or a methanesulfonate.

Advantageous Effects of the Invention

According to the process of the present invention, it is possible to efficiently produce an anthranilamide compound having a bromine at the 3-position of pyrazole, or its salt, and such a compound is useful as a pesticide in agricultural and horticultural fields.

BEST MODE FOR CARRYING OUT THE INVENTION

Now, the process for producing an anthranilamide compound or its salt of the present invention will be described in detail.

The anthranilamide compound of the formula (I) or its salt can be produced in accordance with the following reaction [A] to [C]:

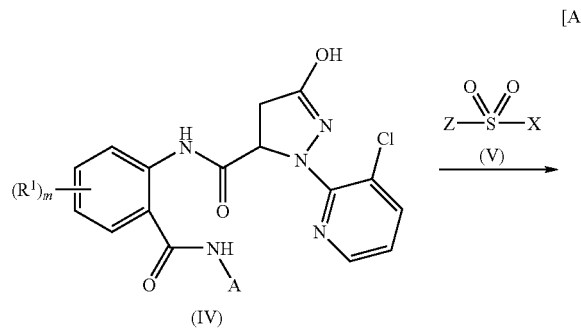

wherein X is a chlorine atom or a bromine atom, $R^1$, A, Z and m are as defined above.

The reaction [A] can be carried out, usually, by reacting the compound of the formula (IV) with at least an equimolar amount of the compound of the formula (V) in the presence of a base and a solvent.

The compound of the formula (IV) to be used for this reaction may, for example, be N-(4-chloro-2-(1-cyclopropylethylcarbamoyl)-6-methylphenyl)-1-(3-chloropyridin-2-yl)-3-hydroxy-4,5-dihydro-1H-pyrazole)-5-carboxamide, N-(2-bromo-4-chloro-6-(1-cyclopropylethylcarbamoyl)phenyl)-1-(3-chloropyridin-2-yl)-3-hydroxy-4,5-dihydro-1H-pyrazole-5-carboxamide, N-(4-chloro-2-(1-cyclopropylethylcarbamoyl)phenyl)-1-(3-chloropyridin-2-yl)-3-hydroxy-4,5-dihydro-1H-pyrazole-5-carboxamide, N-(4-chloro-2-(cyclopropylmethylcarbamoyl)-6-methylphenyl)-1-(3-chloropyridin-2-yl)-3-hydroxy-4,5-dihydro-1H-pyrazole)-5-carboxamide, N-(2-bromo-4-chloro-6-(cyclopropylmethylcarbamoyl)phenyl)-1-(3-chloropyridin-2-yl)-3-hydroxy-4,5-dihydro-1H-pyrazole-5-carboxamide, N-(4-chloro-2-(cyclopropylmethylcarbamoyl)phenyl)-1-(3-chloropyridin-2-yl)-3-hydroxy-4,5-dihydro-1H-pyrazole-5-carboxamide, N-(-4-chloro-2-methyl-6-(methylcarbamoyl)phenyl)-1-(3-chloropyridin-2-yl)-3-hydroxy-4,5-dihydro-1H-pyrazole-5-carboxamide or 1-(3-chloropyridin-2-yl)-N-(4-cyano-2-methyl-6-(methylcarbamoyl)phenyl)-3-hydroxy-4,5-dihydro-1H-pyrazole-5-carboxamide.

The compound of the formula (V) may, for example, be 2-nitrobenzenesulfonyl chloride, 3-nitrobenzenesulfonyl chloride, 4-nitrobenzenesulfonyl chloride, 2-pyridylsulfonyl chloride, 3-pyridylsulfonyl chloride, 4-pyridylsulfonyl chloride, 2-nitrobenzenesulfonyl bromide, 3-nitrobenzenesulfonyl bromide, 4-nitrobenzenesulfonyl bromide, 2-pyridylsulfonyl bromide, 3-pyridylsulfonyl bromide or 4-pyridylsulfonyl bromide.

As the base, one or more types may suitably be selected from, for example, inorganic bases such as lithium hydroxide, sodium hydroxide, potassium hydroxide, calcium hydroxide, lithium carbonate, sodium carbonate and potassium carbonate; alkali metal alkoxides such as sodium t-butoxide and potassium t-butoxide; alkali metal hydrides such as sodium hydride and potassium hydride; and tertiary amines such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 1 to 5 times by mol, preferably from 1 to 3 times by mol, to the compound of the formula (IV).

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; ketones such as acetone, methyl ethyl ketone and cyclohexanone; and polar aprotic solvents such as acetonitrile, propionitrile, N,N-dimethylformamide and dimethyl sulfoxide.

The reaction [A] can be carried out usually at from −20 to 120° C., preferably at from −10 to 80° C., and the reaction time is usually from about 0.1 to about 10 hours.

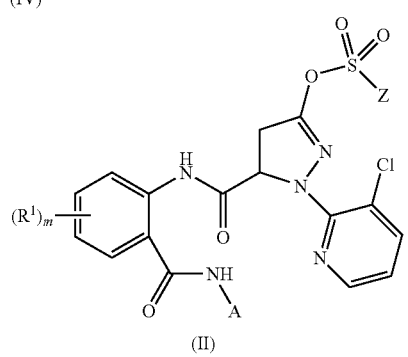

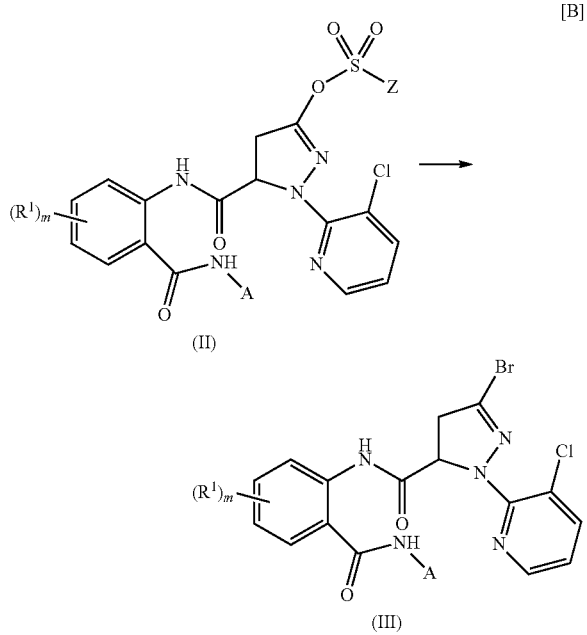

wherein R¹, A, Z and m are as defined above.

The reaction [B] can be carried out, usually, by reacting the compound of the formula (II) with at least an equimolar amount of a brominating agent in the presence of a solvent. The amount of the brominating agent is preferably from 1 to 5 times by mol, to the compound of the formula (II).

The compound of the formula (II) to be used in this reaction may, for example, be 5-(4-chloro-2-(1-cyclopropylethylcarbamoyl)-6-methylphenylcarbamoyl)-1-(3-chloropyridin-2-yl)-4,5-dihydro-1H-pyrazol-3-yl2-nitrobenzene sulfonate, 5-(2-bromo-4-chloro-6-(1-cyclopropylethylcarbamoyl)phenylcarbamoyl)-1-(3-chloropyridin-2-yl)-4,5-dihydro-1H-pyrazol-3-yl2-nitrobenzene sulfonate, 5-(4-chloro-2-(1-cyclopropylethylcarbamoyl)phenylcarbamoyl)-1-(3-chloropyridin-2-yl)-4,5-dihydro-1H-pyrazol-3-yl2-nitrobenzene sulfonate, 5-(4-chloro-2-(cyclopropylmethylcarbamoyl)-6-methylphenylcarbamoyl)-1-(3-chloropyridin-2-yl)-4,5-dihydro-1H-pyrazol-3-yl2-nitrobenzene sulfonate, 5-(2-bromo-4-chloro-6-(cyclopropylmethylcarbamoyl)phenylcarbamoyl)-1-(3-chloropyridin-2-yl)-4,5-dihydro-1H-pyrazol-3-yl2-nitrobenzene sulfonate, 5-(4-chloro-2-(cyclopropylmethylcarbamoyl)phenylcarbamoyl)-1-(3-chloropyridin-2-yl)-4,5-dihydro-1H-pyrazol-3-yl2-nitrobenzene sulfonate, 5-(4-chloro-6-methyl-2-(methylcarbamoyl)phenylcarbamoyl)-1-(3-chloropyridin-2-yl)-4,5-dihydro-1H-pyrazol-3-yl2-nitrobenzene sulfonate, 5-(4-cyano-6-methyl-2-(methylcarbamoyl)phenylcarbamoyl)-1-(3-chloropyridin-2-yl)-4,5-dihydro-1H-pyrazol-3-yl2-nitrobenzene sulfonate, 5-(4-chloro-2-(1-cyclopropylethylcarbamoyl)-6-methylphenylcarbamoyl)-1-(3-chloropyridin-2-yl)-4,5-dihydro-1H-pyrazol-3-yl3-nitrobenzene sulfonate, 5-(2-bromo-4-chloro-6-(1-cyclopropylethylcarbamoyl)phenylcarbamoyl)-1-(3-chloropyridin-2-yl)-4,5-dihydro-1H-pyrazol-3-yl3-nitrobenzene sulfonate, 5-(4-chloro-2-(1-cyclopropylethylcarbamoyl)phenylcarbamoyl)-1-(3-chloropyridin-2-yl)-4,5-dihydro-1H-pyrazol-3-yl3-nitrobenzene sulfonate, 5-(4-chloro-2-(cyclopropylmethylcarbamoyl)-6-methylphenylcarbamoyl)-1-(3-chloropyridin-2-yl)-4,5-dihydro-1H-pyrazol-3-yl3-nitrobenzene sulfonate, 5-(2-bromo-4-chloro-6-(cyclopropylmethylcarbamoyl)phenylcarbamoyl)-1-(3-chloropyridin-2-yl)-4,5-dihydro-1H-pyrazol-3-yl3-nitrobenzene sulfonate, 5-(4-chloro-2-(cyclopropylmethylcarbamoyl)phenylcarbamoyl)-1-(3-chloropyridin-2-yl)-4,5-dihydro-1H-pyrazol-3-yl3-nitrobenzene sulfonate, 5-(4-chloro-6-methyl-2-(methylcarbamoyl)phenylcarbamoyl)-1-(3-chloropyridin-2-yl)-4,5-dihydro-1H-pyrazol-3-yl3-nitrobenzene sulfonate, 5-(4-cyano-6-methyl-2-(methylcarbamoyl)phenylcarbamoyl)-1-(3-chloropyridin-2-yl)-4,5-dihydro-1H-pyrazol-3-yl3-nitrobenzene sulfonate, 5-(4-chloro-2-(1-cyclopropylethylcarbamoyl)-6-methylphenylcarbamoyl)-1-(3-chloropyridin-2-yl)-4,5-dihydro-1H-pyrazol-3-yl4-nitrobenzene sulfonate, 5-(2-bromo-4-chloro-6-(1-cyclopropylethylcarbamoyl)phenylcarbamoyl)-1-(3-chloropyridin-2-yl)-4,5-dihydro-1H-pyrazol-3-yl4-nitrobenzene sulfonate, 5-(4-chloro-2-(1-cyclopropylethylcarbamoyl)phenylcarbamoyl)-1-(3-chloropyridin-2-yl)-4,5-dihydro-1H-pyrazol-3-yl4-nitrobenzene sulfonate, 5-(4-chloro-2-(cyclopropylmethylcarbamoyl)-6-methylphenylcarbamoyl)-1-(3-chloropyridin-2-yl)-4,5-dihydro-1H-pyrazol-3-yl4-nitrobenzene sulfonate, 5-(2-bromo-4-chloro-6-(cyclopropylmethylcarbamoyl)phenylcarbamoyl)-1-(3-chloropyridin-2-yl)-4,5-dihydro-1H-pyrazol-3-yl4-nitrobenzene sulfonate, 5-(4-chloro-2-(cyclopropylmethylcarbamoyl)phenylcarbamoyl)-1-(3-chloropyridin-2-yl)-4,5-dihydro-1H-pyrazol-3-yl4-nitrobenzene sulfonate, 5-(4-chloro-6-methyl-2-(methylcarbamoyl)phenylcarbamoyl)-1-(3-chloropyridin-2-yl)-4,5-dihydro-1H-pyrazol-3-yl4-nitrobenzene sulfonate, 5-(4-cyano-6-methyl-2-(methylcarbamoyl)phenylcarbamoyl)-1-(3-chloropyridin-2-yl)-4,5-dihydro-1H-pyrazol-3-yl4-nitrobenzene sulfonate, 5-(4-chloro-2-(1-cyclopropylethylcarbamoyl)-6-methylphenylcarbamoyl)-1-(3-chloropyridin-2-yl)-4,5-dihydro-1H-pyrazol-3-yl2-pyridyl sulfonate, 5-(2-bromo-4-chloro-6-(1-cyclopropylethylcarbamoyl)phenylcarbamoyl)-1-(3-chloropyridin-2-yl)-4,5-dihydro-1H-pyrazol-3-yl2-pyridyl sulfonate, 5-(4-chloro-2-(1-cyclopropylethylcarbamoyl)phenylcarbamoyl)-1-(3-chloropyridin-2-yl)-4,5-dihydro-1H-pyrazol-3-yl2-pyridyl sulfonate, 5-(4-chloro-2-(cyclopropylmethylcarbamoyl)-6-methylphenylcarbamoyl)-1-(3-chloropyridin-2-yl)-4,5-dihydro-1H-pyrazol-3-yl2-pyridyl sulfonate, 5-(2-bromo-4-chloro-6-(cyclopropylmethylcarbamoyl)phenylcarbamoyl)-1-(3-chloropyridin-2-yl)-4,5-dihydro-1H-pyrazol-3-yl2-pyridyl sulfonate, 5-(4-chloro-2-(cyclopropylmethylcarbamoyl)phenylcarbamoyl)-1-(3-chloropyridin-2-yl)-4,5-dihydro-1H-pyrazol-3-yl2-pyridyl sulfonate, 5-(4-chloro-6-methyl-2-(methylcarbamoyl)phenylcarbamoyl)-1-(3-chloropyridin-2-yl)-4,5-dihydro-1H-pyrazol-3-yl2-pyridyl sulfonate, 5-(4-cyano-6-methyl-2-(methylcarbamoyl)phenylcarbamoyl)-1-(3-chloropyridin-2-yl)-4,5-dihydro-1H-pyrazol-3-yl2-pyridyl sulfonate, 5-(4-chloro-2-(1-cyclopropylethylcarbamoyl)-6-methylphenylcarbamoyl)-1-(3-chloropyridin-2-yl)-4,5-dihydro-1H-pyrazol-3-yl3-pyridyl sulfonate, 5-(2-bromo-4-chloro-6-(1-cyclopropylethylcarbamoyl)phenylcarbamoyl)-1-(3-chloropyridin-2-yl)-4,5-dihydro-1H-pyrazol-3-yl3-pyridyl sulfonate, 5-(4-chloro-2-(1-cyclopropylethylcarbamoyl)phenylcarbamoyl)-1-(3-chloropyridin-2-yl)-4,5-dihydro-1H-pyrazol-3-yl3-pyridyl sulfonate, 5-(4-chloro-2-(cyclopropylmethylcarbamoyl)-6-methylphenylcarbamoyl)-1-(3-chloropyridin-2-yl)-4,5-dihydro-1H-pyrazol-3-yl3-pyridyl sulfonate, 5-(2-bromo-4- chloro-6-(cyclopropylmethylcarbamoyl)phenylcarbamoyl)-1-(3-chloropyridin-2-yl)-4,5-dihydro-1H-pyrazol-3-yl3-pyridyl sulfonate, 5-(4-chloro-2-(cyclopropylmethylcarbamoyl)phenylcarbamoyl)-1-(3-chloropyridin-2-yl)-4,5-dihydro-1H-pyrazol-3-yl3-pyridyl sulfonate, 5-(4-chloro-6-methyl-2-(methylcarbamoyl)phenylcarbamoyl)-1-(3-chloropyridin-2-yl)-4,5-dihydro-1H-pyrazol-3-yl3-pyridyl sulfonate, 5-(4-cyano-6-methyl-2-(methylcarbamoyl)phenylcarbamoyl)-1-(3-chloropyridin-2-yl)-4,5-dihydro-1H-pyrazol-3-yl3-pyridyl sulfonate, 5-(4-chloro-2-(1-cyclopropylethylcarbamoyl)-6-methylphenylcarbamoyl)-1-(3-chloropyridin-2-yl)-4,5-dihydro-1H-pyrazol-3-yl4-pyridyl sulfonate, 5-(2-bromo-4-chloro-6-(1-cyclopropylethylcarbamoyl)phenylcarbamoyl)-1-(3-chloropyridin-2-yl)-4,5-dihydro-1H-pyrazol-3-yl4-pyridyl sulfonate, 5-(4-chloro-2-(1-cyclopropylethylcarbamoyl)phenylcarbamoyl)-1-(3-chloropyridin-2-yl)-4,5-dihydro-1H-pyrazol-3-yl4-pyridyl sulfonate, 5-(4-chloro-2-(cyclopropylmethylcarbamoyl)-6-methylphenylcarbamoyl)-1-(3-chloropyridin-2-yl)-4,5-dihydro-1H-pyrazol-3-yl4-pyridyl sulfonate, 5-(2-bromo-4-chloro-6-(cyclopropylmethylcarbamoyl)phenylcarbamoyl)-1-(3-chloropyridin-2-yl)-4,5-dihydro-1H-pyrazol-3-yl4-pyridyl sulfonate, 5-(4-chloro-2-(cyclopropylmethylcarbamoyl)phenylcarbamoyl)-1-(3-chloropyridin-2-yl)-4,5-dihydro-1H-pyrazol-3-yl4-pyridyl sulfonate, 5-(4-chloro-6-methyl-2-(methylcarbamoyl)phenylcarbamoyl)-1-(3-chloropyridin-2-yl)-4,5-dihydro-1H-pyrazol-3-yl4-pyridyl sulfonate or 5-(4-cyano-6-methyl-2-(methylcarbamoyl)phenylcarbamoyl)-1-(3-chloropyridin-2-yl)-4,5-dihydro-1H-pyrazol-3-yl4-pyridyl sulfonate.

As the brominating agent, one or more types may suitably be selected from, for example, hydrogen bromide; metal bromides such as sodium bromide, potassium bromide, lithium bromide, magnesium bromide, calcium bromide, barium bromide, aluminum bromide, phosphorus tribromide and phosphorus pentabromide; and ammonium bromide salts such as ammonium bromide, tetramethylammonium bromide, tetraethylammonium bromide and tetra n-butylammonium bromide. Hydrogen bromide can be generated by reacting a metal bromide or an ammonium bromide salt with an acid such as sulfuric acid. The reaction [B] may be carried out by generating hydrogen bromide in the reaction system by such a method.

The solvent may be any solvent so long as it is inert to the reaction. For example, one or more types may suitably be selected from, for example, ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; polar aprotic solvents such as acetone, methyl ethyl ketone, cyclohexanone, acetonitrile, propionitrile, N,N-dimethylformamide, dimethyl sulfoxide, hexamethylphosphoric triamide, sulfolane, dimethylacetamide and N-methylpyrrolidone; protic solvents such as acetic acid; and water.

The reaction [B] can be carried out usually at from −20 to 150° C., preferably at from 0 to 100° C., and the reaction time is usually from about 0.1 to about 24 hours.

[C]

(III)

(I)

wherein $R^1$, A and m are as defined above.

The reaction [C] can be carried out, usually, by reacting the compound of the formula (III) with an oxidizing agent in the presence of a solvent, and by this reaction, it is possible to produce the desired anthranilamide compound of the formula (I).

The compound of the formula (III) to be used in this reaction may, for example, be 3-bromo-N-(4-chloro-2-(1-cyclopropylethylcarbamoyl)-6-methylphenyl)-1-(3-chloropyridin-2-yl)-4,5-dihydro-1H-pyrazole-5-carboxamide, 3-bromo-N-(2-bromo-4-chloro-6-(1-cyclopropylethylcarbamoyl)phenyl)-1-(3-chloropyridin-2-yl)-4,5-dihydro-1H-pyrazole-5-carboxamide, 3-bromo-N-(4-chloro-2-(1-cyclopropylethylcarbamoyl)phenyl)-1-(3-chloropyridin-2-yl)-4,5-dihydro-1H-pyrazole-5-carboxamide, 3-bromo-N-(4-chloro-2-(cyclopropylmethylcarbamoyl)-6-methylphenyl)-1-(3-chloropyridin-2-yl)-4,5-dihydro-1H-pyrazole-5-carboxamide, 3-bromo-N-(2-bromo-4-chloro-6-(cyclopropylmethylcarbamoyl)phenyl)-1-(3-chloropyridin-2-yl)-4,5-dihydro-1H-pyrazole-5-carboxamide, 3-bromo-N-(4-chloro-2-(cyclopropylmethylcarbamoyl)phenyl)-1-(3-chloropyridin-2-yl)-4,5-dihydro-1H-pyrazole-5-carboxamide, 3-bromo-N-(4-chloro-2-methyl-6-(methylcarbamoyl)phenyl)-1-(3-chloropyridin-2-yl)-4,5-dihydro-1H-pyrazole-5-carboxamide or 3-bromo-1-(3-chloropyridin-2-yl)-N-(4-cyano-2-methyl-6-(methylcarbamoyl)phenyl)-4,5-dihydro-1H-pyrazole-5-carboxamide.

The oxidizing agent may, for example, be 2,3-dichloro-5,6-dicyano-1,4-benzoquinone, chloranil, o-chloranil, hydrogen peroxide, ammonium peroxydisulfate, sodium peroxydisulfate, potassium peroxydisulfate, potassium permanganate, OXONE (tradename), sodium hypochlorite, sodium chlorite, benzoyl peroxide, tert-butyl hydroperoxide or oxygen. The oxidizing agent can be used in an amount of from 1 to 10 times by mol, preferably from 1 to 4 times by mol, to the compound of the formula (III).

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; esters such as methyl acetate, ethyl acetate and propyl acetate; ketones such as acetone, methyl ethyl ketone and cyclohexanone; polar aprotic solvents such as acetonitrile, propionitrile, N,N-dimethylformamide, dimethyl sulfoxide, hexamethylphosphoric triamide, sulfolane, dimethylacetamide and N-methylpyrrolidone; acetic acid and water.

The reaction [C] can be carried out usually at from 0 to 150° C., preferably at from 20 to 100° C., and the reaction time is usually from about 0.5 to about 50 hours.

The compound of the formula (IV) to be used in the reaction [A] can be produced in accordance with the reaction [D]:

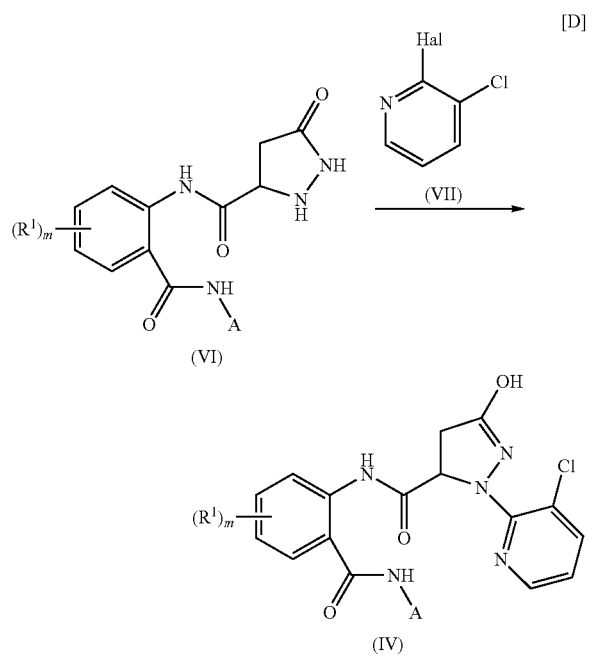

wherein Hal is a fluorine atom, a chlorine atom, a bromide atom or an iodine atom, and $R^1$, A and m are as defined above.

The reaction [D] can be carried out usually by reacting the compound of the formula (VI) with the compound of the formula (VII) in the presence of a base and a solvent in an inert gas atmosphere.

The compound of the formula (VI) may, for example, be N-(4-chloro-2-(1-cyclopropylethylcarbamoyl)-6-methylphenyl)-5-oxopyrazolidine-3-carboxamide, N-(2-bromo-4-chloro-6-(1-cyclopropylethylcarbamoyl)phenyl)-5-oxopyrazolidine-3-carboxamide, N-(4-chloro-2-(1-cyclopropylethylcarbamoyl)phenyl)-5-oxopyrazolidine-3-carboxamide, N-(4-chloro-2-(cyclopropylmethylcarbamoyl)-6-methylphenyl)-5-oxopyrazolidine-3-carboxamide, N-(2-bromo-4-chloro-6-(cyclopropylmethylcarbamoyl)phenyl)-5-oxopyrazolidine-3-carboxamide, N-(4-chloro-2-(cyclopropylmethylcarbamoyl)phenyl)-5-oxopyrazolidine-3-carboxamide, N-(4-chloro-2-methyl-6-(methylcarbamoyl)phenyl)-5-oxopyrazolidine-3-carboxamide, or N-(4-cyano-2-methyl-6-(methylcarbamoyl)phenyl)-5-oxopyrazolidine-3-carboxamide.

The inert gas may be a gas inert to the reaction, such as nitrogen or argon.

As the base, one or more types may suitably be selected from, for example, inorganic bases such as sodium hydroxide, lithium hydroxide, potassium hydroxide, calcium hydroxide, sodium carbonate, potassium carbonate and cesium carbonate; alkali metal alkoxides such as sodium t-butoxide, potassium t-butoxide, sodium ethoxide and sodium methoxide; alkali metal hydrides such as sodium hydride and potassium hydride; and organic bases such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base may be used in an amount of from 1 to 5 times by mol, preferably from 1 to 3.5 times by mol, to the compound of the formula (VI).

The solvent may be any solvent so long as it is inert to the reaction. For example, one or more types may suitably be selected from, for example, ethers such as tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; ketones such as acetone, methyl ethyl ketone and cyclohexanone; and polar aprotic solvents such as acetonitrile, propionitrile, N,N-dimethylformamide, dimethyl sulfoxide, hexamethylphosphoric triamide, sulfolane, dimethylacetamide and N-methylpyrrolidone.

The reaction [D] can be carried out usually at from 0 to 150° C., preferably at from 30 to 100° C., and the reaction time is usually from about 0.5 to about 50 hours.

The compound of the above formula (VI) can be produced usually by reacting the compound of the formula (VIII) with hydrazine in the presence of a solvent (reaction (E)).

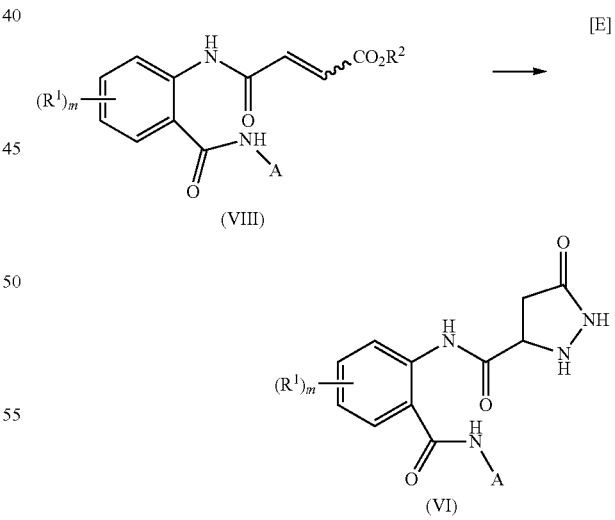

wherein $R^2$ is alkyl; and $R^1$, A and m are as defined above.

The alkyl for $R^2$ may be linear or branched. Its specific example may, for example, be $C_{1-6}$ alkyl such as methyl, ethyl, propyl, isopropyl, butyl, tert-butyl, pentyl or hexyl.

The compound of the formula (VIII) has cis- or trans-isomers, and it may be any one of such isomers or a mixture thereof.

The compound of the formula (VIII) may, for example, be methyl 4-(4-chloro-2-(1-cyclopropylethylcarbamoyl)-6-methylphenylamino)-4-oxocrotonate, ethyl 4-(4-chloro-2-(1-cyclopropylethylcarbamoyl)-6-methylphenylamino)-4-oxocrotonate, methyl 4-(2-bromo-4-chloro-6-(1-cyclopropylethylcarbamoyl)phenylamino)-4-oxocrotonate, ethyl 4-(2-bromo-4-chloro-6-(1-cyclopropylethylcarbamoyl)phenylamino)-4-oxocrotonate, methyl 4-(4-chloro-2-(1-cyclopropylethylcarbamoyl)phenylamino)-4-oxocrotonate, ethyl 4-(4-chloro-2-(1-cyclopropylethylcarbamoyl)phenylamino)-4-oxocrotonate, methyl 4-(4-chloro-2-(cyclopropylmethylcarbamoyl)-6-methylphenylamino)-4-oxocrotonate, ethyl 4-(4-chloro-2-(cyclopropylmethylcarbamoyl)-6-methylphenylamino)-4-oxocrotonate, methyl 4-(2-bromo-4-chloro-6-(cyclopropylmethylcarbamoyl)phenylamino)-4-oxocrotonate, ethyl 4-(2-bromo-4-chloro-6-(cyclopropylmethylcarbamoyl)phenylamino)-4-oxocrotonate, methyl 4-(4-chloro-2-(cyclopropylmethylcarbamoyl)phenylamino)-4-oxocrotonate, ethyl 4-(4-chloro-2-(cyclopropylmethylcarbamoyl)phenylamino)-4-oxocrotonate, methyl 4-(4-chloro-2-methyl-6-(methylcarbamoyl)phenylamino)-4-oxocrotonate, ethyl 4-(4-chloro-2-methyl-6-(methylcarbamoyl)phenylamino)-4-oxocrotonate, methyl 4-(4-cyano-2-methyl-6-(methylcarbamoyl)phenylamino)-4-oxocrotonate, ethyl 4-(4-cyano-2-methyl-6-(methylcarbamoyl)phenylamino)-4-oxocrotonate, methyl 4-(4-chloro-2-(1-cyclopropylethylcarbamoyl)-6-methylphenylamino)-4-oxoisocrotonate, ethyl 4-(4-chloro-2-(1-cyclopropylethylcarbamoyl)-6-methylphenylamino)-4-oxoisocrotonate, methyl 4-(2-bromo-4-chloro-6-(1-cyclopropylethylcarbamoyl)phenylamino)-4-oxoisocrotonate, ethyl 4-(2-bromo-4-chloro-6-(1-cyclopropylethylcarbamoyl)phenylamino)-4-oxoisocrotonate, methyl 4-(4-chloro-2-(1-cyclopropylethylcarbamoyl)phenylamino)-4-oxoisocrotonate, ethyl 4-(4-chloro-2-(1-cyclopropylethylcarbamoyl)phenylamino)-4-oxoisocrotonate, methyl 4-(4-chloro-2-(cyclopropylmethylcarbamoyl)-6-methylphenylamino)-4-oxoisocrotonate, ethyl 4-(4-chloro-2-(cyclopropylmethylcarbamoyl)-6-methylphenylamino)-4-oxoisocrotonate, methyl 4-(2-bromo-4-chloro-6-(cyclopropylmethylcarbamoyl)phenylamino)-4-oxoisocrotonate, ethyl 4-(2-bromo-4-chloro-6-(cyclopropylmethylcarbamoyl)phenylamino)-4-oxoisocrotonate, methyl 4-(4-chloro-2-(cyclopropylmethylcarbamoyl)phenylamino)-4-oxoisocrotonate, ethyl 4-(4-chloro-2-(cyclopropylmethylcarbamoyl)phenylamino)-4-oxoisocrotonate, methyl 4-(4-chloro-2-methyl-6-(methylcarbamoyl)phenylamino)-4-oxoisocrotonate, ethyl 4-(4-chloro-2-methyl-6-(methylcarbamoyl)phenylamino)-4-oxoisocrotonate, methyl 4-(4-cyano-2-methyl-6-(methylcarbamoyl)phenylamino)-4-oxoisocrotonate, or ethyl 4-(4-cyano-2-methyl-6-(methylcarbamoyl)phenylamino)-4-oxoisocrotonate.

Hydrazine can be used in an amount of from 0.9 to 3 times by mol, preferably from 1 to 1.5 times by mol, to the compound of the formula (VIII).

The solvent may be any solvent so long as it is inert to the reaction. For example, one or more types may suitably be selected from, for example, protic solvents such as methanol, ethanol, propanol, butanol, isopropyl alcohol, 2-methyl-2-propanol and water; ethers such as diethyl ether, butyl methyl ether, tetrahydrofuran, dioxane and dimethoxyethane; halogenated hydrocarbons such as chlorobenzene, dichlorobenzene, dichloromethane, chloroform, carbon tetrachloride, dichloroethane, trichloroethane and dichloroethylene; aromatic hydrocarbons such as benzene, toluene and xylene; aliphatic hydrocarbons such as pentane, hexane, heptane, octane and cyclohexane; and polar aprotic solvents such as N,N-dimethylformamide, dimethyl sulfoxide, hexamethylphosphoric triamide, sulfolane, N,N-dimethylacetamide and N-methylpyrrolidone.

This reaction can be carried out usually at from −10 to 150° C., preferably at from 0 to 100° C., and the reaction time is usually from about 0.2 to about 20 hours.

The compound of the above formula (VIII) can be produced in accordance with [F]:

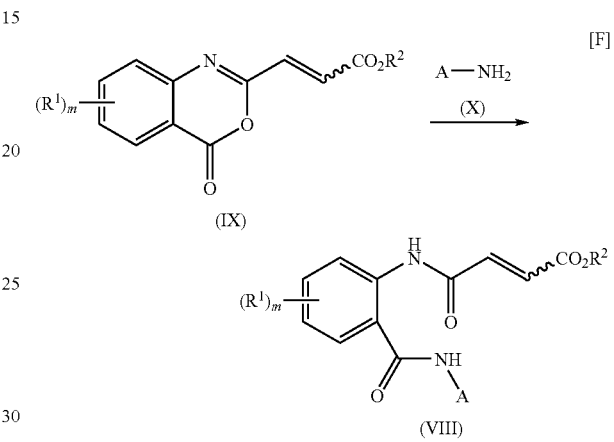

wherein $R^1$, $R^2$, A and m are as defined above.

The compounds (VIII) and (IX) have cis- and trans-isomers, and each compound may be any one of such isomers or a mixture thereof.

The reaction [F] can be carried out usually by reacting the compound of the formula (IX) with the compound of the formula (X) in the presence of a solvent or by reacting the compound of the formula (IX) with a salt of the compound of the formula (X) in the presence of a solvent and a base.

The compound of the formula (IX) to be used in this reaction may, for example, be methyl (E)-3-(6-chloro-8-methyl-4-oxo-4H-benzo[d][1,3]oxazin-2-yl)acrylate, ethyl (E)-3-(6-chloro-8-methyl-4-oxo-4H-benzo[d][1,3]oxazin-2-yl) acrylate, methyl (E)-3-(8-bromo-6-chloro-4-oxo-4H-benzo[d][1,3]oxazin-2-yl)acrylate, ethyl (E)-3-(8-bromo-6-chloro-4-oxo-4H-benzo[d][1,3]oxazin-2-yl)acrylate, methyl (E)-3-(6-chloro-4-oxo-4H-benzo[d][1,3]oxazin-2-yl)acrylate, ethyl (E)-3-(6-chloro-4-oxo-4H-benzo[d][1,3]oxazin-2-yl) acrylate, methyl (E)-3-(6-cyano-8-methyl-4-oxo-4H-benzo[d][1,3]oxazin-2-yl)acrylate, ethyl (E)-3-(6-cyano-8-methyl-4-oxo-4H-benzo[d][1,3]oxazin-2-yl)acrylate, methyl (Z)-3-(6-chloro-8-methyl-4-oxo-4H-benzo[d][1,3]oxazin-2-yl) acrylate, ethyl (Z)-3-(6-chloro-8-methyl-4-oxo-4H-benzo[d][1,3]oxazin-2-yl)acrylate, methyl (Z)-3-(8-bromo-6-chloro-4-oxo-4H-benzo[d][1,3]oxazin-2-yl)acrylate, ethyl (Z)-3-(8-bromo-6-chloro-4-oxo-4H-benzo[d][1,3]oxazin-2-yl) acrylate, methyl (Z)-3-(6-chloro-4-oxo-4H-benzo[d][1,3] oxazin-2-yl)acrylate, ethyl (Z)-3-(6-chloro-4-oxo-4H-benzo[d][1,3]oxazin-2-yl)acrylate, methyl (Z)-3-(6-cyano-8-methyl-4-oxo-4H-benzo[d][1,3]oxazin-2-yl)acrylate or ethyl (Z)-3-(6-cyano-8-methyl-4-oxo-4H-benzo[d][1,3]oxazin-2-yl)acrylate.

Further, as the compound of the formula (X), 1-cyclopropylethylamine, 1-cyclobutylethylamine, cyclopropylmethylamine or methylamine may, for example, be used. As the salt of the compound of the formula (X), a salt of an inorganic acid such as a hydrochloride or a sulfate; or a salt of an organic acid such as an acetate or a methanesulfonate may, for example, be used. The compound of the formula (X) or its salt may be used in an equimolar amount or more, preferably from 1 to 5 times by mol to the compound of the formula (IX).

In a case where a salt of the compound of the formula (X) is used, it is preferred to further use a base. As such a base, one or more types may suitably be selected from, for example, inorganic bases such as sodium hydroxide, potassium hydroxide, sodium carbonate, potassium carbonate, sodium hydrogen carbonate and potassium hydrogen carbonate; alkali metal hydrides such as sodium hydride and potassium hydride; alkali metal alkoxides such as sodium t-butoxide, potassium t-butoxide, sodium ethoxide and sodium methoxide; and organic bases such as trimethylamine, triethylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene and 1,4-diazabicyclo[2.2.2]octane. The base can be used in an amount of from 0.7 to 5 times by mol, preferably from 1 to 1.5 times by mol, to the salt of the compound of the formula (X).

The solvent may be any solvent so long as it is inert to the reaction. For example, one or more types may suitably be selected from, for example, ethers such as diethyl ether, tetrahydrofuran, dioxane and dimethoxyethane; halogenated hydrocarbons such as methylene chloride, chloroform, carbon tetrachloride and chlorobenzene; aromatic hydrocarbons such as benzene, toluene and xylene; aliphatic hydrocarbons such as pentane, hexane, heptane, octane and cyclohexane; and polar aprotic solvents such as acetonitrile, N,N-dimethylformamide, dimethylacetamide, N-methylpyrrolidone, dimethyl sulfoxide, hexamethylphosphoric triamide and sulfolane.

This reaction can be carried out usually at from −20 to 120° C., preferably from −10 to 80° C., and the reaction time is usually from about 0.1 to about 24 hours.

The compounds obtained by the above-described reactions [A] to [F] may have optical isomers or geometrical isomers in some cases, and such isomers and mixtures thereof are both covered by the present invention. Further, in the present invention, various isomers other than those mentioned above may be included within the scope of the common knowledge in this technical field. Further, depending upon the type of such an isomer, the chemical structure may be different from the structures in the above reaction formulae, but it is obvious to one skilled in the part that such a structure is in isomeric relation and thus falls within the scope of the present invention.

Further, the present invention includes the following processes.

(1) A process for producing the compound of the formula (II) by the above reaction [A].

(2) A process for producing the compound of the formula (III) by the above reaction [B].

(3) A process for producing the compound of the formula (III) by the above reactions [A] and [B] and producing the compound of the formula (I) by the above reaction [C].

(4) A process for producing the compound of the formula (IV) by the above reaction [D] and producing the compound of the formula (I) by the above reactions [A], [B] and [C].

(5) A process for producing the compound of the formula (VI) by the above reaction [E] and producing the compound of the formula (I) by the above reactions [D], [A], [B] and [C].

(6) A process for producing the compound of the formula (VIII) by the above reaction [F] and producing the compound of the formula (I) by the above reactions [E], [D], [A], [B] and [C].

EXAMPLES

Now, the present invention will be described in detail with reference to Examples, but it should be understood that the present invention is by no means restricted thereto.

Example 1

Preparation (1) of N-(4-chloro-2-(1-cyclopropylethylcarbamoyl)phenyl)-3-bromo-1-(3-chloropyridin-2-yl)-4,5-dihydro-1H-pyrazole-5-carboxamide (1) Preparation of 5-(4-chloro-2-(1-cyclopropylethylcarbamoyl)phenylcarbamoyl)-1-(3-chloropyridin-2-yl)-4,5-dihydro-1H-pyrazol-3-yl2-nitrobenzene sulfonate 1.0 g of N-(4-chloro-2-(1-cyclopropylethylcarbamoyl)phenyl)-1-(3-chloropyridin-2-yl)-3-hydroxy-4,5-dihydro-1H-pyrazole-5-carboxamide was dissolved in 10 mL of chloroform, and under cooling with ice, 280 mg of triethylamine and then 580 mg of 2-nitrobenzenesulfonyl chloride were added, followed by stirring overnight. To the reaction liquid, water and ethyl acetate were added, followed by stirring and extraction with ethyl acetate. Then, concentration under reduced pressure was carried out to obtain a crude product. The crude product was purified by silica gel column chromatography (eluent: n-hexane/ethyl acetate=1/1 (volume ratio, the same applies hereinafter.)) to obtain 1.36 g of the desired product in a paste form. $^1$H-NMR of the obtained purified product is shown below (the same applies hereinafter).

$^1$H-NMR (400 MHz, CDCl$_3$) δ: 11.39 (d, 1H), 8.49 (dd, 1H), 8.43 (m, 1H), 8.11 (dd, 1H), 7.78-7.90 (m, 4H), 7.58 (d, 2H), 7.34-7.40 (m, 2H), 6.85 (m, 1H), 6.0 (t, 1H), 5.56 (ddd, 1H), 3.36-3.52 (m, 3H), 1.21 (dd, 3H), 0.9 (m, 1H), 0.2-0.7 (m, 4H)

(2) Preparation of N-(4-chloro-2-(1-cyclopropylethylcarbamoyl)phenyl)-3-bromo-1-(3-chloropyridin-2-yl)-4,5-dihydro-1H-pyrazole-5-carboxamide 400 mg of 5-(4-chloro-2-(1-cyclopropylethylcarbamoyl)phenylcarbamoyl)-1-(3-chloropyridin-2-yl)-4,5-dihydro-1H-pyrazol-3-yl2-nitrobenzene sulfonate was dissolved in 0.7 mL of acetic acid, and 0.3 mL of a 33 mass % hydrogen bromide acetic acid solution was dropwise added, followed by stirring for about one hour. After completion of the reaction, ethyl acetate, water and 2 mL of 1 N sodium hydroxide were added, followed by stirring and extraction with ethyl acetate. Then, concentration under reduced pressure was carried out to obtain a crude product. The crude product was purified by silica gel column chromatography (eluent: n-hexane/ethyl acetate=3/2) to obtain 310 mg of the desired product in a paste form.

$^1$H-NMR (300 MHz, CDCl$_3$) δ: 11.48 (d, 1H), 8.50 (dd, 1H), 8.13 (t, 1H), 7.67 (d, 1H), 7.4 (ds, 2H), 6.9 (m, 1H), 6.03 (t, 1H), 5.50 (ddd, 1H), 3.35-3.58 (m, 3H), 1.17 (d, 3H), 0.85 (m, 1H), 0.23-0.6 (m, 4H)

Example 2

Preparation (2) of N-(4-chloro-2-(1-cyclopropylethylcarbamoyl)phenyl)-3-bromo-1-(3-chloropyridin-2-yl)-4,5-dihydro-1H-pyrazole-5-carboxamide (1) Preparation of 5-(4-chloro-2-(1-cyclopropylethylcarbamoyl)phenylcarbamoyl)-1-(3-chloropyridin-2-yl)-4,5-dihydro-1H-pyrazol-3-yl3-nitrobenzene sulfonate 1.0 g of N-(4-chloro-2-(1-cyclopropylethylcarbamoyl) phenyl)-1-(3-chloropyridin-2-yl)-3-hydroxy-4,5-dihydro-1H-pyrazole-5-carboxamide was dissolved in 10 mL of tetrahydrofuran, and under cooling with ice, 280 mg of triethylamine and then 570 mg of 3-nitrobenzenesulfonyl chloride were added, followed by stirring for about 5.5 hours. To the reaction liquid, water and ethyl acetate were added, followed by stirring and extraction with ethyl acetate. Then, concentration under reduced pressure was carried out to obtain a crude product. The crude product was purified by silica gel column chromatography (eluent: n-hexane/ethyl acetate=1/1) to obtain 1.31 g of the desired product in a paste form.

$^1$H-NMR (400 MHz, CDCl$_3$) δ: 11.42 (d, 1H), 8.93 (s, 1H), 8.55 (dd, 1H), 8.47 (m, 3H), 8.11 (m, 1H), 7.81 (dd, 1H), 7.61 (d, 1H), 7.35-7.39 (m, 2H), 6.86 (m, 1H), 6.0 (t, 1H), 5.55 (ddd, 1H), 3.33-3.48 (m, 3H), 1.21 (dd, 3H), 0.9 (m, 1H), 0.2-0.7 (m, 4H)

(2) Preparation of N-(4-chloro-2-(1-cyclopropylethylcarbamoyl)phenyl)-3-bromo-1-(3-chloropyridin-2-yl)-4,5-dihydro-1H-pyrazole-5-carboxamide 400 mg of 5-(4-chloro-2-(1-cyclopropylethylcarbamoyl)phenylcarbamoyl)-1-(3-chloropyridin-2-yl)-4,5-dihydro-1H-pyrazol-3-yl3-nitrobenzene sulfonate was dissolved in 0.7 mL of acetic acid, and 0.3 mL of a 33 mass % hydrogen bromide acetic acid solution was dropwise added, followed by stirring for about 1.5 hours. After completion of the reaction, ethyl acetate, water and 1.8 mL of 1 N sodium hydroxide were added, followed by stirring and extraction with ethyl acetate. Then, concentration under reduced pressure was carried out to obtain a crude product. The crude product was purified by silica gel column chromatography (eluent: n-hexane/ethyl acetate=3/2) to obtain 320 mg of the desired product in a paste form.

Example 3

Preparation (3) of N-(4-chloro-2-(1-cyclopropylethylcarbamoyl)phenyl)-3-bromo-1-(3-chloropyridin-2-yl)-4,5-dihydro-1H-pyrazole-5-carboxamide (1) Preparation of 5-(4-chloro-2-(1-cyclopropylethylcarbamoyl)phenylcarbamoyl)-1-(3-chloropyridin-2-yl)-4,5-dihydro-1H-pyrazol-3-yl4-nitrobenzene sulfonate 1.0 g of N-(4-chloro-2-(1-cyclopropylethylcarbamoyl) phenyl)-1-(3-chloropyridin-2-yl)-3-hydroxy-4,5-dihydro-1H-pyrazole-5-carboxamide was dissolved in 10 mL of tetrahydrofuran, and under cooling with ice, 330 mg of triethylamine and then 570 mg of 4-nitrobenzenesulfonyl chloride were added, followed by stirring for about 3 hours. To the reaction liquid, water and ethyl acetate were added, followed by stirring and extraction with ethyl acetate. Then, concentration under reduced pressure was carried out to obtain a crude product. The crude product was purified by silica gel column chromatography (eluent: n-hexane/ethyl acetate=1/1) to obtain 1.34 g of the desired product in a paste form.

$^1$H-NMR (400 MHz, CDCl$_3$) δ: 11.43 (d, 1H), 8.47 (dd, 1H), 8.36 (dd, 2H), 8.11 (m, 1H), 7.61 (d, 1H), 7.36-7.40 (m, 2H), 6.87 (m, 1H), 6.0 (t, 1H), 5.54 (ddd, 1H), 3.37-3.47 (m, 3H), 1.23 (dd, 3H), 0.9 (m, 1H), 0.2-0.7 (m, 4H)

(2) Preparation of N-(4-chloro-2-(1-cyclopropylethylcarbamoyl)phenyl)-3-bromo-1-(3-chloropyridin-2-yl)-4,5-dihydro-1H-pyrazole-5-carboxamide 400 mg of 5-(4-chloro-2-(1-cyclopropylethylcarbamoyl)phenylcarbamoyl)-1-(3-chloropyridin-2-yl)-4,5-dihydro-1H-pyrazol-3-yl4-nitrobenzene sulfonate was dissolved in 0.7 mL of acetic acid, and 0.3 mL of a 33 mass % hydrogen bromide acetic acid solution was dropwise added, followed by stirring for about 1 hour. After completion of the reaction, ethyl acetate, water and 2 mL of 1 N sodium hydroxide were added, followed by stirring and extraction with ethyl acetate. Then, concentration under reduced pressure was carried out to obtain a crude product. The crude product was purified by silica gel column chromatography (eluent: n-hexane/ethyl acetate=3/2) to obtain 310 mg of the desired product in a paste form.

Example 4

Preparation (4) of N-(4-chloro-2-(1-cyclopropylethylcarbamoyl)phenyl)-3-bromo-1-(3-chloropyridin-2-yl)-4,5-dihydro-1H-pyrazole-5-carboxamide (1) Preparation of 5-(4-chloro-2-(1-cyclopropylethylcarbamoyl)phenylcarbamoyl)-1-(3-chloropyridin-2-yl)-4,5-dihydro-1H-pyrazol-3-yl3-pyridine sulfonate 1.0 g of N-(4-chloro-2-(1-cyclopropylethylcarbamoyl) phenyl)-1-(3-chloropyridin-2-yl)-3-hydroxy-4,5-dihydro-1H-pyrazole-5-carboxamide was dissolved in 10 mL of tetrahydrofuran, and under cooling with ice, 550 mg of triethylamine and then 460 mg of 3-pyridinesulfonyl chloride were added, followed by stirring for about one hour. Then, 25 mg of 4-dimethylaminopyridine was added, followed by further stirring for about 30 minutes. To the reaction liquid, water and ethyl acetate were added, followed by stirring and extraction with ethyl acetate. Then, concentration under reduced pressure was carried out to obtain a crude product. The crude product was purified by silica gel column chromatography (eluent: n-hexane/ethyl acetate=1/2) to obtain 1.36 g of the desired product in a paste form.

$^1$H-NMR (400 MHz, CDCl$_3$) δ: 11.45 (d, 1H), 9.30 (s, 1H), 8.90 (d, 1H), 8.43-8.50 (m, 2H), 8.11 (dd, 1H), 7.61 (d, 1H), 7.53 (m, 1H), 7.35-7.38 (m, 2H), 6.86 (m, 1H), 6.2 (t, 1H), 5.54 (ddd, 1H), 3.36-3.48 (m, 3H), 1.21 (dd, 3H), 0.9 (m, 1H), 0.2-0.7 (m, 4H)

(2) Preparation of N-(4-chloro-2-(1-cyclopropylethylcarbamoyl)phenyl)-3-bromo-1-(3-chloropyridin-2-yl)-4,5-dihydro-1H-pyrazole-5-carboxamide 400 mg of 5-(4-chloro-2-(1-cyclopropylethylcarbamoyl)phenylcarbamoyl)-1-(3-chloropyridin-2-yl)-4,5-dihydro-1H-pyrazol-3-yl3-pyridine sulfonate was dissolved in 0.7 mL of acetic acid, and 0.4 mL of a 33 mass % hydrogen bromide acetic acid solution was dropwise added, followed by stirring for about 1 hour. After completion of the reaction, ethyl acetate, water and 2.8 mL of 1 N sodium hydroxide were added, followed by stirring and extraction with ethyl acetate. Then, concentration under reduced pressure was carried out to obtain a crude product. The crude product was purified by silica gel column chromatography (eluent: n-hexane/ethyl acetate=3/2) to obtain 330 mg of the desired product in a paste form.

Example 5

Preparation (5) of N-(4-chloro-2-(1-cyclopropylethylcarbamoyl)phenyl)-3-bromo-1-(3-chloropyridin-2-yl)-4,5-dihydro-1H-pyrazole-5-carboxamide 400 mg of 5-(4-chloro-2-(1-cyclopropylethylcarbamoyl) phenylcarbamoyl)-1-(3-chloropyridin-2-yl)-4,5-dihydro-1H-pyrazol-3-yl-4-nitrobenzene sulfonate was dissolved in 0.7 mL of acetic acid, and 0.2 mL of a 47 mass % hydrogen bromide aqueous solution was dropwise added, followed by stirring for about 6 days. After completion of the reaction, ethyl acetate, water and 2 mL of 1 N sodium hydroxide were added, followed by stirring and extraction with ethyl acetate. Then, concentration under reduced pressure was carried out to obtain a crude product. The crude product was purified by silica gel column chromatography (eluent: n-hexane/ethyl acetate=3/2) to obtain 250 mg of the desired product in a paste form.

Example 6

Preparation (6) of N-(4-chloro-2-(1-cyclopropylethylcarbamoyl)phenyl)-3-bromo-1-(3-chloropyridin-2-yl)-4,5-dihydro-1H-pyrazole-5-carboxamide 10.0 g of 5-(4-chloro-2-(1-cyclopropylethylcarbamoyl)phenylcarbamoyl)-1-(3-chloropyridin-2-yl)-4,5-dihydro-1H-pyrazol-3-yl2-nitrobenzene sulfonate was dissolved in 30 mL of acetic acid, and after adding 2.4 g of sodium bromide, 1.3 mL of 98 mass % concentrated sulfuric acid was dropwise added at room temperature. After completion of the dropwise addition, heating was carried out at an internal temperature of from 40 to 50° C. for about two hours. After completion of the reaction, the reaction solution was dropwise added into 60 mL of a 8 mass % sodium hydroxide aqueous solution to obtain 8.3 g of the desired product in a crystal form.

Comparative Example 1

Preparation (7) of N-(4-chloro-2-(1-cyclopropylethylcarbamoyl)phenyl)-3-bromo-1-(3-chloropyridin-2-yl)-4,5-dihydro-1H-pyrazole-5-carboxamide 400 mg of 5-(4-chloro-2-(1-cyclopropylethylcarbamoyl)phenylcarbamoyl)-1-(3-chloropyridin-2-yl)-4,5-dihydro-1H-pyrazol-3-yl4-methylbenzene sulfonate was dissolved in 0.7 mL of acetic acid, and 0.3 mL of a 33 mass % hydrogen bromide acetic acid solution was dropwise added, followed by stirring for about 2.5 hours. After completion of the reaction, ethyl acetate, water and 2 mL of 1 N sodium hydroxide were added, followed by stirring and extraction with ethyl acetate. Then, concentration under reduced pressure was carried out to obtain a crude product. The crude product was purified by silica gel column chromatography (eluent: n-hexane/ethyl acetate=3/2) to obtain 260 mg of the desired product in a paste form.

Comparative Example 2

Preparation (8) of N-(4-chloro-2-(1-cyclopropylethylcarbamoyl)phenyl)-3-bromo-1-(3-chloropyridin-2-yl)-4,5-dihydro-1H-pyrazole-5-carboxamide 400 mg of 5-(4-chloro-2-(1-cyclopropylethylcarbamoyl)phenylcarbamoyl)-1-(3-chloropyridin-2-yl)-4,5-dihydro-1H-pyrazol-3-yl4-methylbenzene sulfonate was dissolved in 0.7 mL of acetic acid, and 0.2 mL of a 47 mass % hydrogen bromide aqueous solution was dropwise added, followed by stirring for about 6 days. After completion of the reaction, ethyl acetate, water and 2 mL of 1 N sodium hydroxide were added, followed by stirring and extraction with ethyl acetate. Then, concentration under reduced pressure was carried out to obtain a crude product. The crude product was purified by silica gel column chromatography (eluent: n-hexane/ethyl acetate=3/2) to obtain 180 mg of the desired product in a paste form.

The yields in the above bromination reactions are shown in Table 1. As shown in Table 1, the bromination reactions employing the compounds of the formula (II) of the present invention proceeded with high yields as compared with the conventional technique.

TABLE 1

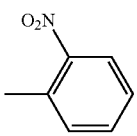

| | Z | Brominating condition (brominating agent) | Yield |
|---|---|---|---|
| Ex. 1 | 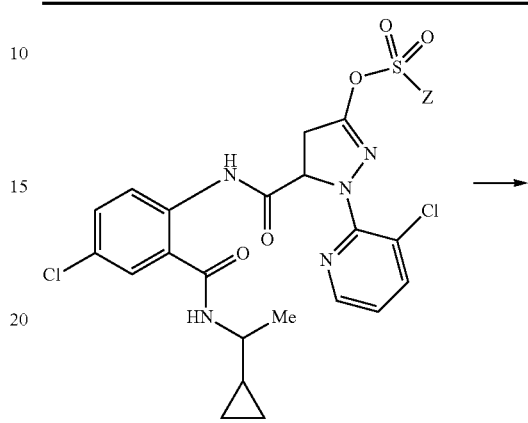 | 33 mass % hydrogen bromide/acetic acid | 96% |
| Ex. 2 | 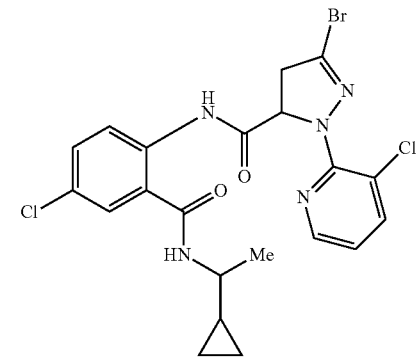 | 33 mass % hydrogen bromide/acetic acid | 99% |
| Ex. 3 | 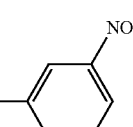 | 33 mass % hydrogen bromide/acetic acid | 96% |
| Ex. 4 | 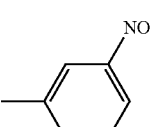 | 33 mass % hydrogen bromide/acetic acid | 95% |
| Ex. 5 | 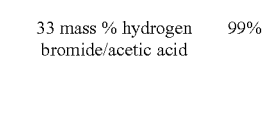 | 47 mass % hydrogen bromide aqueous solution/acetic acid | 77% |

TABLE 1-continued

| Comp. Ex. 1 | ⌬—Me | 33 mass % hydrogen bromide/acetic acid | 76% |
| Comp. Ex. 2 | ⌬—Me | 47 mass % hydrogen bromide aqueous solution/acetic acid | 53% |

Example 7

Preparation of 3-bromo-N-(4-chloro-2-(1-cyclopropylethylcarbamoyl)phenyl)-1-(3-chloropyridin-2-yl)-1H-pyrazole-5-carboxamide 0.24 g of potassium peroxodisulfate and 0.02 g of sulfuric acid were added to 3 ml of an N,N-dimethylformamide solution containing 0.10 g of 3-bromo-N-(4-chloro-2-(1-cyclopropylethylcarbamoyl)phenyl)-1-(3-chloropyridin-2-yl)-4,5-dihydro-1H-pyrazole-5-carboxamide, followed by heating and refluxing. After 1.5 hours, the reaction liquid was left to cool and introduced into 10 ml of water, and then ethyl acetate was added, followed by extraction. The organic layer (the ethyl acetate layer) was washed with a saturated sodium chloride aqueous solution, and dried over anhydrous sodium sulfate. The solvent was distilled off under reduced pressure, and the residue was purified by silica gel column chromatography (eluent: n-hexane/ethyl acetate=1/0 to 1/2) to obtain 0.09 g of the desired product (melting point: 231-233° C.).
$^1$H-NMR (400 MHz, CDCl$_3$) δ: 12.25 (br, 1H), 8.48 (dd, 1H), 8.44 (d, 1H), 7.89 (dd, 1H), 7.45-7.33 (m, 3H), 7.01 (s, 1H), 6.23 (d, 1H), 3.57-3.54 (m, 1H), 1.34 (d, 3H), 0.95-0.90 (m, 1H), 0.63-0.51 (m, 2H), 0.43-0.32 (m, 2H)

Example 8

Preparation of N-(4-chloro-2-(1-cyclopropylethylcarbamoyl)phenyl)-1-(3-chloropyridin-2-yl)-3-hydroxy-4,5-dihydro-1H-pyrazole-5-carboxamide (1) Preparation of methyl 4-(4-chloro-2-(1-cyclopropylethylcarbamoyl)phenylamino)-4-oxocrotonate A mixed solution of 0.73 g of 1-cyclopropylethylamine hydrochloride and 0.91 g of triethylamine in 12 ml of acetonitrile was stirred at room temperature for one hour. Then, to the mixed solution, 0.53 g of crude crystals of methyl (E)-3-(6-chloro-4-oxo-4H-benzo[d][1,3]oxazin-2-yl)acrylate were added at room temperature and reacted for 3 hours at room temperature. To the reaction liquid, water was added, and then ethyl acetate was added for extraction. The organic layer was washed with a saturated sodium chloride aqueous solution and dried over anhydrous sodium sulfate. The solvent was distilled off under reduced pressed, and the residue was purified by silica gel column chromatography (eluent: n-hexane/ethyl acetate=9/1 to 8/2) to obtain 0.22 g of the desired product having a slightly yellow color (melting point: 154.4° C.).
$^1$H-NMR (400 MHz, CDCl$_3$) δ: 11.62 (br, 1H), 8.69-8.66 (m, 1H), 7.46-7.43 (m, 2H), 7.05 (d, 1H), 6.88 (d, 2H), 6.21 (brd, 1H), 3.80 (s, 3H), 3.53-3.48 (m, 1H), 1.32 (d, 3H), 0.96-0.90 (m, 1H), 0.62-0.48 (m, 2H), 0.42-0.36 (m, 1H), 0.34-0.29 (m, 1H)

(2) Preparation of N-(4-chloro-2-(1-cyclopropylethylcarbamoyl)phenyl)-5-oxopyrazolidine-3-carboxamide A mixed liquid of 90 mg of hydrazine monohydrate and 3 ml of ethanol, was added to a mixed liquid of 0.56 g of methyl 4-(4-chloro-2-(1-cyclopropylethylcarbamoyl)phenylamino)-4-oxocrotonate and 3 ml of ethanol, followed by rinsing with 2 ml of ethanol and then by heating and refluxing for 6 hours. The reaction liquid was left to cool, and then, the precipitated crystals were collected by suction filtration, and the crystals were washed with ethanol and air-dried to obtain 0.16 g of the desired product (melting point: 248° C.).
$^1$H-NMR (300 MHz, DMSO-d$_6$) δ: 11.83 (s, 1H), 9.14 (d, 1H), 8.53 (d, 1H), 8.36 (d d, 1H), 7.57 (t, 1H), 7.38 (dd, 1H), 5.99 (dd, 1H), 3.99 (t, 1H), 3.30 (m, 1H), 2.56 (dd, 1H), 2.27-2.32 (m, 1H), 1.04 (q, 3H), 0.81 (m, 1H), 0.00-0.40 (m, 4H)

(3) Preparation of N-(4-chloro-2-(1-cyclopropylethylcarbamoyl)phenyl)-1-(3-chloropyridin-2-yl)-3-hydroxy-4,5-dihydro-1H-pyrazole-5-carboxamide 1.0 g of N-(4-chloro-2-(1-cyclopropylethylcarbamoyl)phenyl)-5-oxopyrazolidine-3-carboxamide was dissolved in 10 mL of N,N-dimethylformamide, and 460 mg of 2,3-dichloropyridine and then 350 mg of sodium hydride were added, followed by stirring at about 70° C. for about 7 hours in a nitrogen atmosphere, and then the reaction liquid was left to cool. To the reaction liquid, water and ethyl acetate were added, followed by stirring and extraction with ethyl acetate. Then, concentration under reduced pressure was carried out to obtain a crude product. The crude product was purified by silica gel column chromatography (eluent: ethyl acetate/ethanol=9/1) to obtain 1.15 g of the desired product (melting point: 165-167° C.).
$^1$H-NMR (300 MHz, CDCl$_3$) δ: 12.17 (s, 1H), 8.58 (d, 1H), 8.25 (dd, 1H), 7.82 (b r, 1H), 7.72 (d, 1H), 7.42 (ds, 2H), 7.10 (dd, 1H), 6.26 (d, 1H), 4.93 (m, 1H), 3.45 (m, 1H), 2.93 (ds, 2H), 1.24 (d, 3H), 0.89 (m, 1H), 0.12-0.64 (m, 4H)

Industrial Applicability

The anthranilamide compound having halogen at the 3-position of pyrazole, or its salt, prepared by the process of the present invention, is useful as a pesticide in agricultural and horticultural fields.

The entire disclosure of Japanese Patent Application No. 2008-106657 filed on Apr. 16, 2008 including specification, claims and abstract is incorporated herein by reference in its entirety.

The invention claimed is:
1. A process for producing an anthranilamide compound represented by formula (I) or its salt:

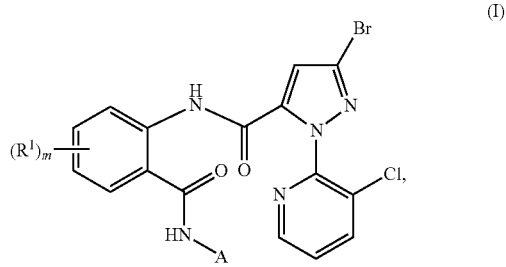

wherein:
R$^1$ is halogen, alkyl, haloalkyl, alkenyl, haloalkenyl, alkynyl, haloalkynyl, alkoxy, haloalkoxy, alkylcarbonyl, haloalkylcarbonyl, alkoxycarbonyl, haloalkoxycarbonyl, nitro, formyl or cyano;
A is an alkyl group which is optionally substituted by Y;

Y is a $C_{3-4}$ cycloalkyl group which is optionally substituted by at least one substituent selected from the group consisting of a halogen, an alkyl group and a haloalkyl group; and m is an integer of from 0 to 4, the process comprising:

(i) reacting a compound represented by formula (II):

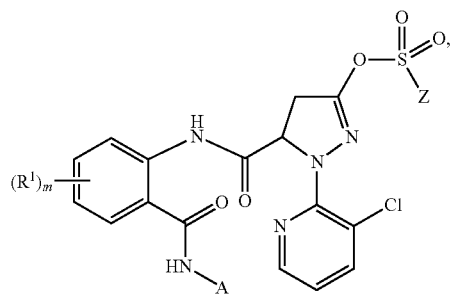

wherein Z is a 2-pyridyl, a 3-pyridyl, a 4-pyridyl or a benzene substituted with a nitro group, with a brominating agent, to produce a compound represented by formula (III):

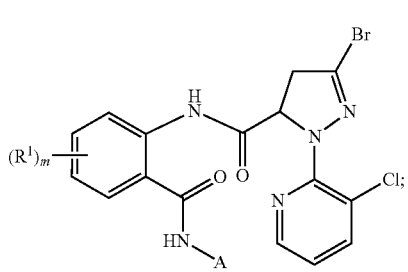

and (ii) reacting the compound of the formula (III) with an oxidizing agent, to obtain the compound of formula (I).

2. The process according to claim 1, wherein compound of formula (II) is reacted (i) with an amount of the brominating agent which is at least equimolar to the compound of the formula (II).

3. The process according to claim 1, wherein the compound of formula (III) is reacted (ii) with an amount of the oxidizing agent that is from 1 to 10 times by mol to that of the compound of the formula (III).

4. The process according to claim 1, wherein the compound of the formula (II) is a compound produced by reacting a compound represented by formula (IV):

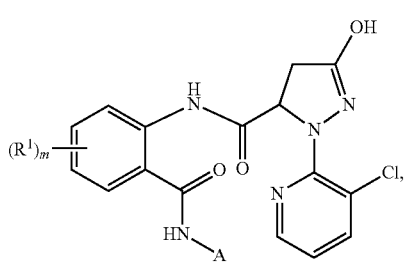

with a compound represented by formula (V):

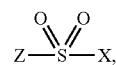

wherein:
X is a chlorine atom or a bromine atom; and
Z is 2-pyridyl, 3-pyridyl, 4-pyridyl or benzene substituted with a nitro group.

5. The process according to claim 1, wherein the compound of the formula (II) is a compound produced by reacting a compound represented by formula (VI):

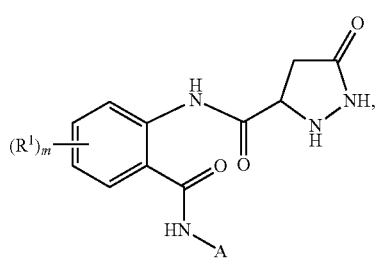

with a compound represented by formula (VII):

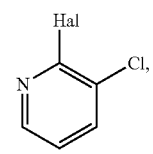

wherein Hal is a fluorine atom, a chlorine atom, a bromine atom or an iodine atom), to produce a compound represented by formula (IV):

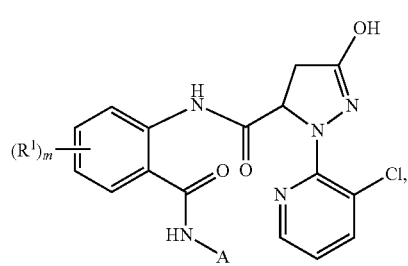

and further reacting the compound of the formula (IV) with a compound represented by formula (V):

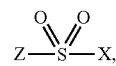

wherein:
X is a chlorine atom or a bromine atom; and
Z is 2-pyridyl, 3-pyridyl, 4-pyridyl or benzene substituted by a nitro group.

6. The process of claim 1, wherein the brominating agent is at least one selected from the group consisting of hydrogen bromide, a metal bromide, and an ammonium bromide salt.

7. The process of claim 1, wherein the brominating agent is hydrogen bromide generated by reacting a metal bromide or an ammonium bromide salt with an acid.

8. The process of claim 1, wherein the reacting (i) occurs in the presence of a solvent (i).

9. The process of claim 8, wherein the solvent (i) is at least one selected from the group consisting of an ether, a halogenated hydrocarbon, an aromatic hydrocarbon, an aliphatic hydrocarbon, an ester, a polar aprotic solvent, a protic solvent and water.

10. The process of claim 1, wherein the reacting (i) occurs at from -20 to 150° C.

11. The process of claim 1, wherein the oxidizing agent is at least one selected from the group consisting of 2,3-dichloro-5,6-dicyano-1,4-benzoquinone, chloranil, o-chloranil, hydrogen peroxide, ammonium peroxydisulfate, sodium peroxydisulfate, potassium peroxydisulfate, potassium permanganate, potassium peroxymonosulfate, sodium hypochlorite, sodium chlorite, benzoyl peroxide, tert-butyl hydroperoxide, and oxygen.

12. The process of claim 1, wherein the reacting (ii) occurs in the presence of a solvent (ii).

13. The process of claim 12, wherein the solvent (ii) is at least one selected from the group consisting of an ether, a halogenated hydrocarbon, an aromatic hydrocarbon, an aliphatic hydrocarbon, an ester, a ketone, a polar aprotic solvent, acetic acid and water.

14. The process of claim 1, wherein the reacting (ii) occurs at from 0 to 150° C.

15. The process of claim 4, comprising reacting the compound of formula (IV) with the compound of formula (V) in the presence of a base, a solvent, or both.

16. The process of claim 15, comprising reacting the compound of formula (IV) with the compound of formula (V) in the presence of a base selected from the group consisting of an inorganic base, an alkali metal alkoxide, an alkali metal hydride, a tertiary amine, a pyridine, and mixtures thereof.

17. The process of claim 5, comprising reacting the compound of formula (VI) with the compound of formula (VII) in the presence of at least one selected from the group consisting of a base, a solvent, and an inert gas atmosphere.

18. The process of claim 17, comprising reacting the compound of formula (VI) with the compound of formula (VII) in the presence of at least one base selected from the group consisting of an inorganic base, an alkali metal alkoxide, an alkali metal hydride and an organic base.

* * * * *